US00PP37432P2

(12) United States Plant Patent
Vermeulen et al.

(10) Patent No.: US PP37,432 P2
(45) Date of Patent: May 19, 2026

(54) ***DRACAENA* PLANT NAMED 'SILINDO'**

(50) Latin Name: ***Dracaena steudneri* Schweinf. ex Engl.**
Varietal Denomination: SILINDO

(71) Applicants: Joost Vermeulen, Lubbeek (BE); Mathijs Vermeulen, Lubbeek (BE)

(72) Inventors: Joost Vermeulen, Lubbeek (BE); Mathijs Vermeulen, Lubbeek (BE)

( * ) Notice: Subject to any disclaimer, the term of this patent is extended or adjusted under 35 U.S.C. 154(b) by 761 days.

(21) Appl. No.: 18/445,497

(22) Filed: Sep. 1, 2023

(51) Int. Cl.
*A01H 5/12* (2018.01)
*A01H 6/12* (2018.01)

(52) U.S. Cl.
USPC ..... Plt./383
CPC ..... *A01H 6/12* (2018.05)

(58) Field of Classification Search
USPC ..... Plt./383
CPC ..... A01H 6/12; A01H 5/12
See application file for complete search history.

*Primary Examiner* — Keith O. Robinson
(74) *Attorney, Agent, or Firm* — Samuel R. McCoy, Jr.

(57) ABSTRACT

A new and distinct *Dracaena* plant named 'SILINDO' which is characterized by large, lightly spiraled foliage born on an unbranched stem, dark green foliage that is centrally striped with golden-yellow and narrowly margined with yellow-green, and the stability of these characteristics from generation to generation.

2 Drawing Sheets

Latin name of the genus and species: The Latin name of the genus and species of the novel variety disclosed herein is *Dracaena steudneri* Schweinf. ex Engl.

Variety denomination: The inventive cultivar of *Dracaena* disclosed herein has been given the variety denomination 'SILINDO'.

BACKGROUND OF THE INVENTION

Parentage: 'SILINDO' is a spontaneous branch mutation of an unnamed *Dracaena steudneri* plant (not patented) which typified the species. The mutation was discovered at a commercial greenhouse in Lubbeek, Belgium in March of 2018. The mutation was initially noted for its dark green, uniquely variegated foliage with yellow longitudinal striping along the central portion of the leaf blades. Said mutation was isolated for further evaluation to confirm the uniformity and stability of the unique characteristics first observed. Upon confirmation of the stability and uniformity of the characteristics, the new plant was selected for commercialization.

Asexual Reproduction: Asexual reproduction of 'SILINDO' is accomplished by way of rooting stem cuttings. Propagation was first performed in March of 2018 at the inventor's commercial greenhouse in Lubbeek, Belgium. Through five subsequent generations, the unique features of this cultivar have proven to be stable and true to type.

SUMMARY OF THE INVENTION

The cultivar 'SILINDO' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'SILINDO'. These characteristics in combination distinguish 'SILINDO' as a new and distinct *Dracaena steudneri* cultivar:

1. *Dracaena* 'SILINDO' exhibits large, lightly spiraled foliage born on a solitary short, unbranched stem; and
2. *Dracaena* 'SILINDO' exhibits dark green foliage that is centrally striped with yellow-green, generally appearing as golden-yellow; and
3. *Dracaena* 'SILINDO' exhibits foliage that is very narrowly margined with yellow-green.

BOTANICAL DESCRIPTION OF THE PLANT

Figure 1:
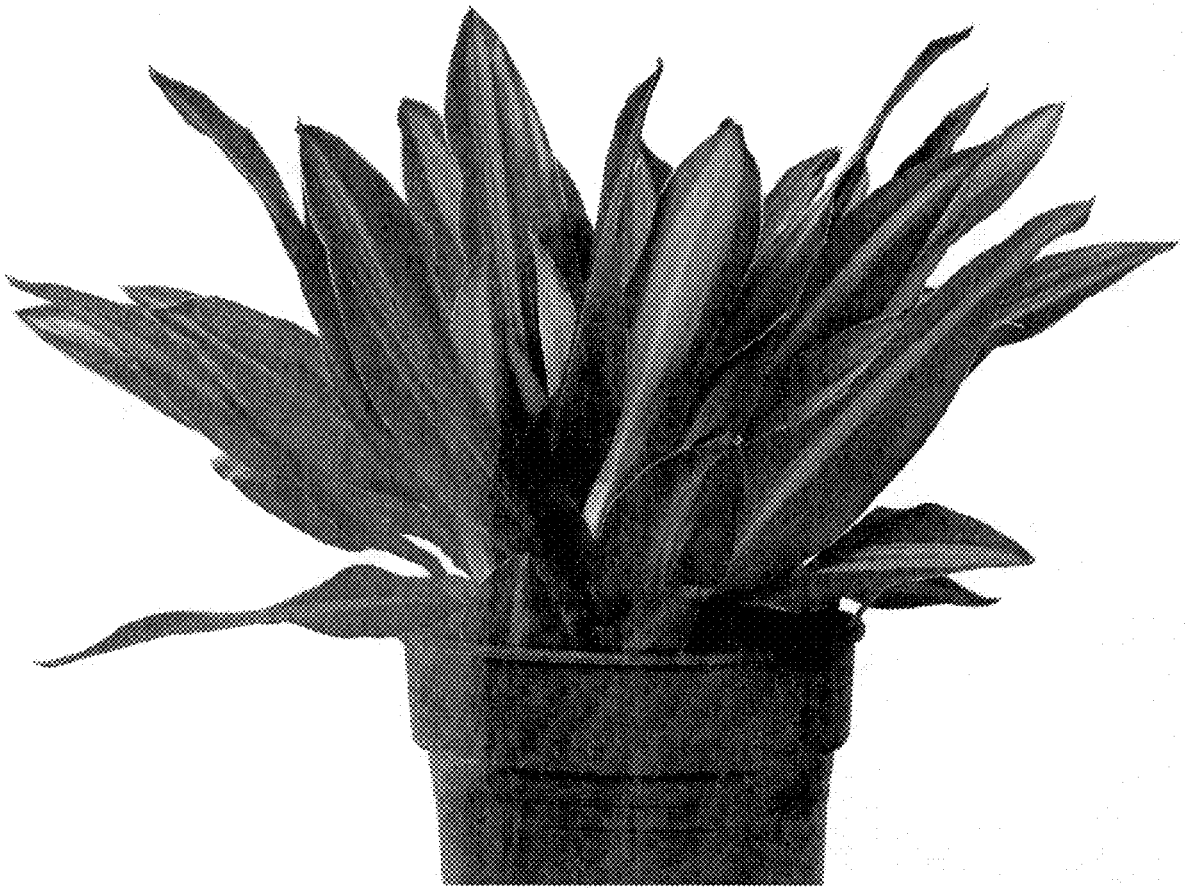
FIG. 1 illustrates, as nearly true as it is reasonably possible to make the same in color photographs of this type, an exemplary plant of 'SILINDO' grown in Lubbeek, Belgium. This plant, grown in a 17 cm nursery container, is approximately 1.5 years old from a rooted young plant.
Figure 2:
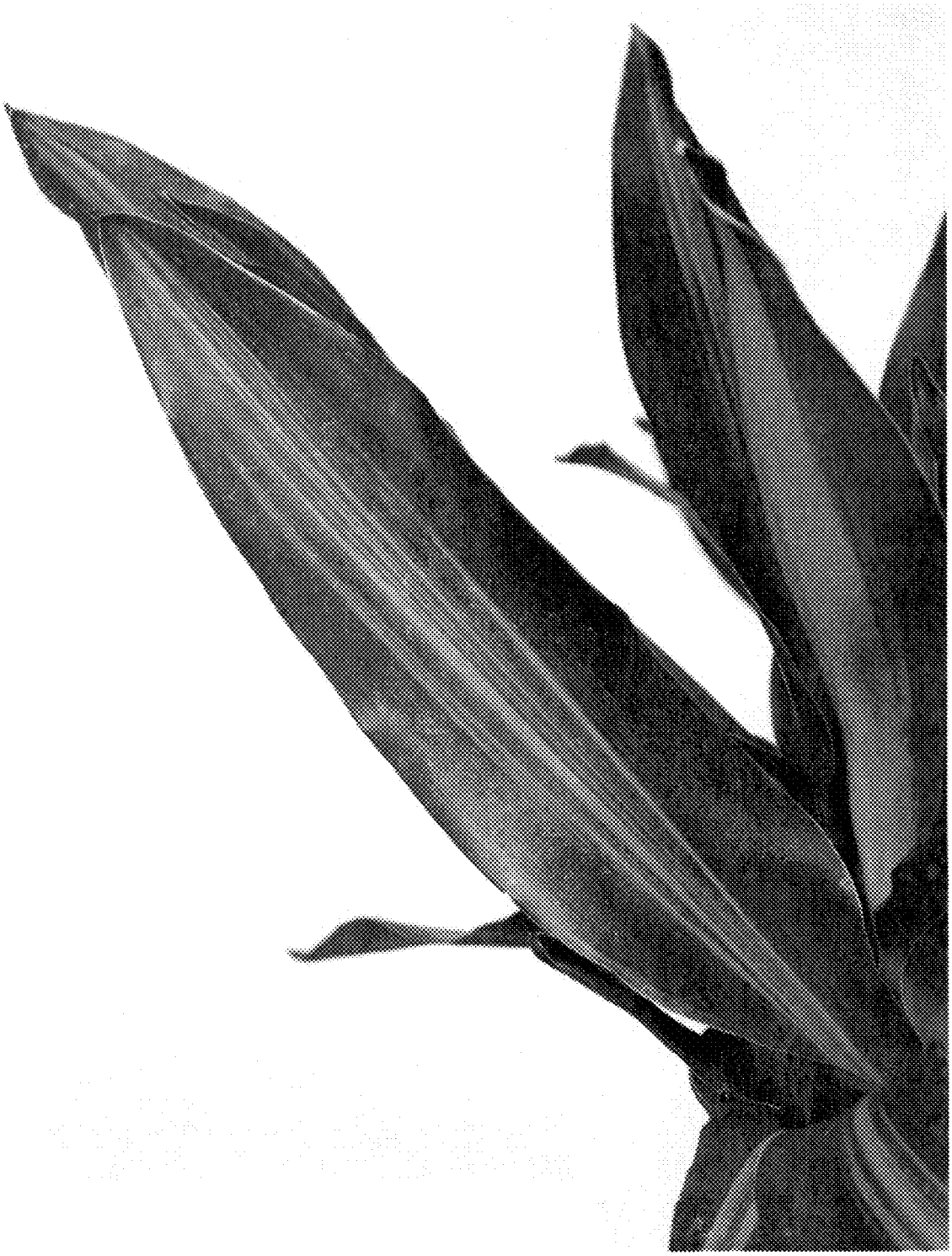
FIG. 2 illustrates, as nearly true as it is reasonably possible to make the same in color photographs of this type, the typical foliage of 'SILINDO'.

The following observations and measurements, made in December of 2022, describe averages from a sample set of six specimens of 1.5-year-old 'SILINDO' plants grown in 17 cm nursery pots in Lubbeek, Belgium. Plants were produced using conventional greenhouse production protocols for *Dracaena* sp. which consisted of growing under shade cloth, regular overhead irrigation, and chemical control of thrips insects. No photoperiodic treatments or artificial light was given to the plants.

Those skilled in the art will appreciate that certain characteristics will vary with older or, conversely, with younger plants. 'SILINDO' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on The Royal Horticultural Socity Colour Chart, The Royal Horticultural Society, London, 2015 (sixth edition).

A botanical description of 'SILINDO' and comparisons with the parent plant and most similar commercial *Dracaena* cultivar known to the inventor are provided below.

Plant description:

*Growth habit.*—Compact, upright evergreen perennial with foliage born on a solitary short, unbranched stem.

*Plant profile.*—Broad obovate.

*Average height from base to top of foliage.*—28.6 cm.

*Average width.*—42.1 cm.

*Plant vigor.*—Moderately vigorous.

*Propagation details.*—Asexual propagation is accomplished by stem cuttings.

*Time to initiate roots.*—Approximately 3 weeks are required to initiate roots at 20 degrees Celsius.

*Time to produce a marketable* 15 *cm potted plant.*—Approximately 10 weeks.

*Disease and pest resistance or susceptibility.*—Neither tolerance nor resistance to normal diseases and pests of *Dracaena steudneri* have been observed.

*Environmental tolerances.*—Adapt to USDA Hardiness Zones 10 through 12 and temperatures as high as 40 degrees Celsius; moderate tolerance to rain and wind.

Root system:

*General.*—Fibrous; freely branched and moderately dense rooting.

*Distribution in the soil profile.*—Shallow to moderately deep.

*Texture.*—Smooth; glabrous.

Stems:

*Branching characteristics.*—Not freely branched in nature; develops lateral branches only when manipulated by man by way of pruning. Naturally produces one main stem arising from the plant's base.

*Attitude.*—Near vertical.

*Strength.*—Very strong.

*Length.*—8.8 cm.

*Diameter.*—Average 1.3 cm.

*Internode length.*—Average 1.3 cm.

*Stem texture.*—Glabrous; smooth.

*Stem luster.*—Slightly glossy.

*Color, developing stems.*—Green-white, nearest to RHS 157A.

*Color, mature stems.*—Yellow-green, nearest to a mixture of RHS 144B and 145C.

*Color at the internodes.*—Yellow-green, nearest to RHS 144A.

Foliage:

*Arrangement.*—Alternate.

*Attachment.*—Sheathed.

*Division.*—Simple.

*Attitude.*—Leaves at an average angle of 60 degrees to the stem.

*Number of leaves per shoot.*—13.

*Lamina.*—Dimensions — 27.5 cm long and 5.9 cm wide, on average. Shape — Lorate. Aspect — Slightly spiraled, with the distalmost portion on the lamina pointing downward at an average angle of minus-10 degrees to the rest of the lamina. Apex — Acute with a short, pungent tip. Base — Sheathed. Sheath — Length — 2.3 cm. Width —1.3 cm. Color, adaxial surface — Green-white, nearest to RHS 157B. Color, abaxial surface — Green-white, nearest to RHS 157A. Margin — Entire; coarse undulation. Texture and luster of adaxial surface — Smooth, glabrous and moderately glossy. Texture and luster of abaxial surface — Smooth, glabrous and very slightly glossy. Color — Juvenile foliage, adaxial surface — Green, nearest to RHS NN137A, and prominently striped with yellow-green along the central zone of the lamina, nearest to a mixture of RHS 145A and 150B. The striping varies from a plurality of narrow, individual stripes to a single, broad stripe, all running from the base to the apex. Laminas are very narrowly margined with yellow-green, nearest to RHS 145A. Juvenile foliage, abaxial surface — Yellow-green, nearest to a mixture of RHS 146B and 147B, and prominently striped with yellow-green along the central zone of the lamina, nearest to a mixture of RHS 145B and 145C. The striping varies from a plurality of narrow, individual stripes to a single, broad stripe, all running from the base to the apex. Laminas are very narrowly margined with yellow-green, nearest to RHS 145A. Mature foliage, adaxial surface — Green, nearest to a mixture of RHS NN137A and 139A, and prominently striped with yellow-green along the central zone of the lamina, nearest to a mixture of RHS 145A and 150B and becoming N144C towards the base. The striping varies from a plurality of narrow, individual stripes to a single, broad stripe, all running from the base to the apex. Laminas are very narrowly margined with yellow-green, nearest to RHS 145A. Mature foliage, abaxial surface — Yellow-green, nearest to a mixture of RHS 146B and 147B, and prominently striped with yellow-green along the central zone of the lamina, nearest to a mixture of RHS 145A, 145B, and 146D. The striping varies from a plurality of narrow, individual stripes to a single, broad stripe, all running from the base to the apex. Laminas are very narrowly margined with yellow-green, nearest to RHS 145A. Venation — Pattern — Parallel. Color, adaxial surface — The main vein yellow-green, nearest to RHS 147B. All other veins are indistinguishable from the surrounding foliage. Color, abaxial surface — The main vein is yellow-green, nearest to RHS 150C. All other veins are indistinguishable from the surrounding foliage.

Inflorescence: To date, flowering has not been observed.

Flower buds: To date, flowering has not been observed.

Flower: To date, flowering has not been observed.

Reproductive organs: To date, flowering has not been observed.

Seed and fruit: To date, flowering has not been observed.

Comparisons with the parent plant: Plants of the new cultivar 'SILINDO' may be distinguished from its parent, an unnamed *Dracaena steudneri* plant (not patented), by the characteristics described in Table 1.

TABLE 1

| Characteristic | 'SILINDO' | The parent. |
|---|---|---|
| Foliage aspect. | Spiraled, with the distal portion curling downward. | Straight; not spiraled or curling downward. |
| Margin undulation | Less undulation. | More undulation. |
| Base color of the foliage. | Uniformly dark green. | Varying shades of green. |
| Variegation of the foliage. | Yellow-green stripes, generally appearing as golden yellow, are present along the central zone of the lamina. Stripes vary from a plurality of narrow, individual stripes to a single, broad stripe, all running from the base to the apex. | No striping is present. |
| Foliage margin coloration. | Narrowly margined yellow-green, generally appearing as golden yellow. | Broadly and irregularly margined golden yellow. |

Plants of the new cultivar 'SILINDO' are similar to the closest known commercial comparator, *Dracaena fragrans* 'Dragreye' (U.S. Pat. No. 32,804), in that both plants have similarly-colored foliage. However, the two plants may be distinguished from one another by the characteristics described in Table 2.

TABLE 2

| Characteristic | 'SILINDO' | 'Dragreye'. |
|---|---|---|
| Foliage size. | Larger than 'Dragreye'. | Smaller than 'SILINDO'. |
| Foliage abundance. | Less abundant. | More abundant. |
| Foliage aspect. | Spiraled, with the distal portion of the lamina slightly curled downward. | Flat with the distal portion of the lamina strongly curled downward. |
| Base color of the foliage. | Uniformly dark green. | Varying shades of light and dark green, yet generally appearing as mid-green. |
| Variegation of the foliage. | Yellow-green stripes, generally appearing as golden yellow, are present along the central zone of the lamina. Stripes vary from a plurality of narrow, individual stripes to a single, broad stripe, all running from the base to the apex. | Varying shades of light and dark green, yet generally appearing as mid-green. |
| Foliage margin coloration. | Narrowly margined yellow-green, generally appearing as golden yellow. | Broadly and irregularly margined golden yellow. |

That which is claimed is:

1. A new and distinct cultivar of *Dracaena* plant named 'SILINDO', substantially as described and illustrated herein.

* * * * *